United States Patent
Soliman

(10) Patent No.: US 10,856,789 B2
(45) Date of Patent: Dec. 8, 2020

(54) HIGHLY-SENSITIVE MUSHROOM METAL-DIELECTRIC SENSOR BACKED BY A METAL GROUND PLANE FOR REFRACTIVE INDEX SENSING

(71) Applicant: The American University in Cairo, New York, NY (US)

(72) Inventor: Ezzeldin Soliman, New Cairo (EG)

(73) Assignee: The American University in Cairo, New York, NY (US)

( * ) Notice: Subject to any disclaimer, the term of this patent is extended or adjusted under 35 U.S.C. 154(b) by 238 days.

(21) Appl. No.: 16/092,842

(22) PCT Filed: Apr. 10, 2017

(86) PCT No.: PCT/US2017/026782
§ 371 (c)(1),
(2) Date: Oct. 11, 2018

(87) PCT Pub. No.: WO2017/180506
PCT Pub. Date: Oct. 19, 2017

(65) Prior Publication Data
US 2019/0125222 A1 May 2, 2019

Related U.S. Application Data

(60) Provisional application No. 62/321,067, filed on Apr. 11, 2016.

(51) Int. Cl.
*A61B 5/1459* (2006.01)
*G01N 21/552* (2014.01)
(Continued)

(52) U.S. Cl.
CPC .......... *A61B 5/1459* (2013.01); *G01N 21/41* (2013.01); *G01N 21/554* (2013.01); *G02F 2/02* (2013.01);
(Continued)

(58) Field of Classification Search
CPC ............... A61B 5/1459; A61B 5/1455; A61B 2562/0233; A61B 2562/0285; G01N 21/554; G01N 21/41
See application file for complete search history.

(56) References Cited

U.S. PATENT DOCUMENTS

2009/0166222 A1* 7/2009 Mirkin ............. G01N 33/54346
204/403.01
2010/0041065 A1 2/2010 Horii
(Continued)

FOREIGN PATENT DOCUMENTS

WO WO2014126927 8/2014

*Primary Examiner* — Eric F Winakur
(74) *Attorney, Agent, or Firm* — Lumen Patent Firm

(57) ABSTRACT

A nano antenna for refractive index sensing is provided that includes a silica substrate, a gold nanodisk sensor element on a first side of the substrate, where the gold nanodisk sensor element includes a silica disk disposed on the substrate and a gold disk disposed on the silica disk, where a diameter of the gold disk is greater than a diameter of the silica disk, where a height of the silica disk is greater than a height of the gold disk, and a gold layer disposed on a second side of the substrate opposite the first side, where the gold layer covers an area as large as said gold nanodisk sensor element.

9 Claims, 7 Drawing Sheets

(51) Int. Cl.
   *G01N 21/41*   (2006.01)
   *G02F 2/02*    (2006.01)
   *H02J 50/27*   (2016.01)

(52) U.S. Cl.
   CPC ............... *A61B 2560/0214* (2013.01); *A61B 2562/0233* (2013.01); *A61B 2562/0285* (2013.01); *G02F 2203/10* (2013.01); *H02J 50/27* (2016.02)

(56) References Cited

U.S. PATENT DOCUMENTS

| | | |
|---|---|---|
| 2012/0021249 A1 | 1/2012 | Shin |
| 2013/0003058 A1 | 1/2013 | Van Dorpe |
| 2014/0045209 A1 | 2/2014 | Chou |

\* cited by examiner

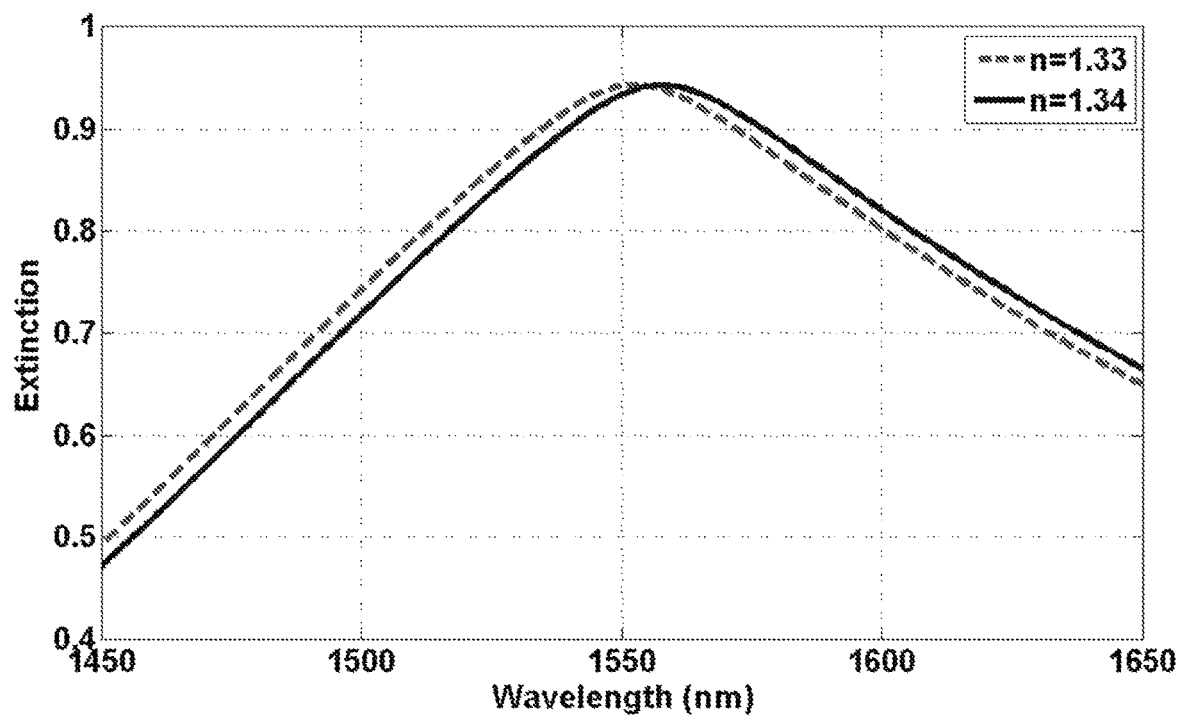
FIG. 3 *Prior Art*
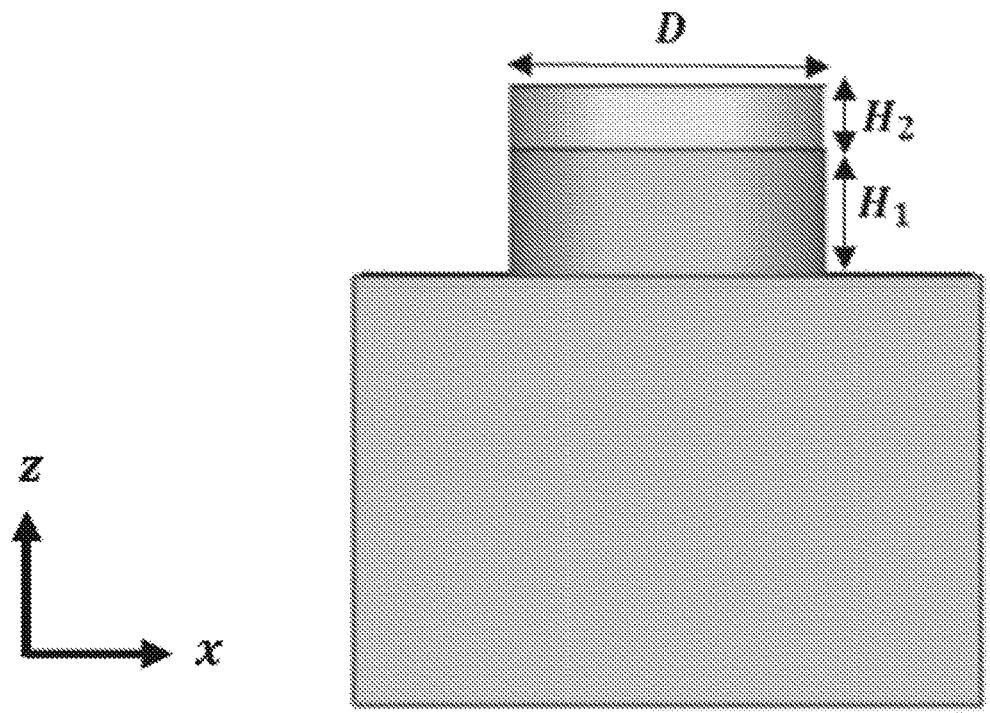
FIG. 4

Gold layer

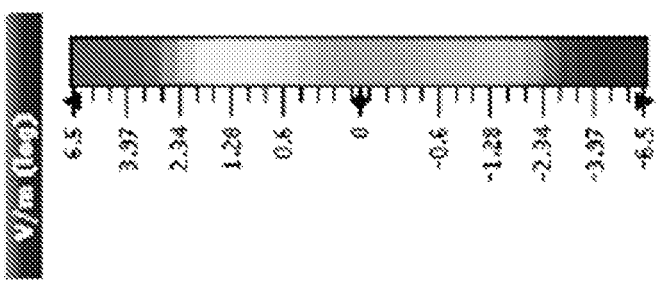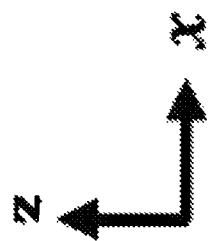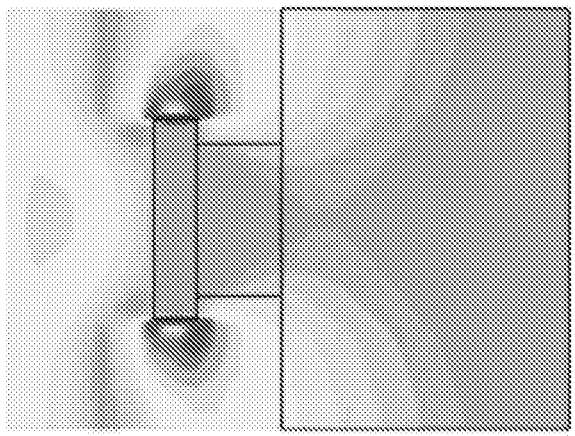
*FIG. 10C*
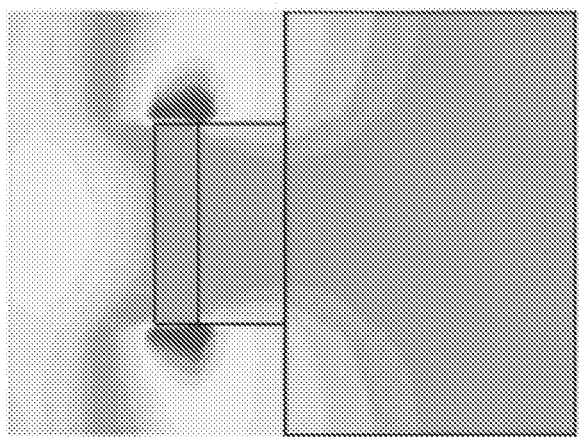
*FIG. 10B*
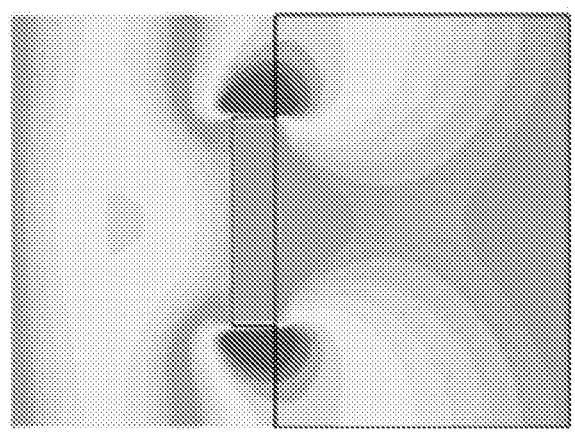
*FIG. 10A*

HIGHLY-SENSITIVE MUSHROOM METAL-DIELECTRIC SENSOR BACKED BY A METAL GROUND PLANE FOR REFRACTIVE INDEX SENSING

CROSS-REFERENCE TO RELATED APPLICATIONS

This application is a 371 of PCT application PCT/US2017/026782 filed Apr. 10, 2017. PCT application PCT/US2017/026782 filed Apr. 10, 2017 claims the benefit of U.S. Provisional application 62/321,067 filed Apr. 11, 2016.

FIELD OF THE INVENTION

The invention relates to refractive index sensing. More specifically, the invention relates to a nano antenna refractive index sensor.

BACKGROUND OF THE INVENTION

During the past decades, the unique optical properties of noble metals have attracted much attention. In the nano particles made up of noble metals, strong interaction at the surface between metal and dielectric causes a collective oscillation in the conduction electrons, which is known as Localized Surface Plasmon Resonance (LSPR). LSPR results in strong electromagnetic field confinement, which opened the gate to many fascinating applications, such as: biomedical sensing, near-field scanning microscopy, surface enhanced spectroscopy, and optical trapping. Plasmonic sensing is one interesting application that has recently attracted a lot of research. With the significant improvements in the nanofabrication techniques, different shapes have been explored as plasmonic sensors, such as: disks, rings, crescents, dipoles, bowties, crosses and cubes. Gold nanodisks are a basic nano structure used for sensing. Due to their symmetric shapes, they are easily fabricated. Various nano disk structures have been reported in literature. Previously, the possibility of tuning the disk diameter for achieving the desired plasmon resonance wavelength was demonstrated. It was shown that while maintaining the height constant, the plasmon resonance wavelength red shifts as the diameter of the disk increases. It was also experimentally proven that the sensitivity of the nanodisk increases from 60 nm/RIU to 200 nm/RIU as the aspect ratio increases where the aspect ratio is defined as the ratio between the diameter and height of the disk. This suggests that for increasing the sensitivity of the gold nano disk, its height should be much smaller than its diameter, which is pre-defined by the desired resonance wavelength. This limits the sensitivity of nano disks since small disk' height means low interaction with the analyte. Another limitation of the nano disks is their rapid field decay away from the metal surface, which imposes relative small volume of interaction between the disk's electromagnetic fields and the analyte.

What is needed is a nano antenna structure that increased the sensitivity via maximizing the region of interaction between the field and analyte.

SUMMARY OF THE INVENTION

To address the needs in the art, a nano antenna for refractive index sensing is provided that includes a silica substrate, a gold nanodisk sensor element on a first side of the substrate, where the gold nanodisk sensor element includes a silica disk disposed on the substrate and a gold disk disposed on the silica disk, where a diameter of the gold disk is greater than a diameter of the silica disk, where a height of the silica disk is greater than a height of the gold disk, and a gold layer disposed on a second side of the substrate opposite the first side, where the gold layer covers an area as large as said gold nanodisk sensor element.

According to one aspect of the invention, the gold nanodisk sensor element includes an array of the gold nanodisk sensor elements, where the gold layer covers an area at least as large as the array of gold nanodisk sensor elements.

In another aspect, the invention further includes an RF antenna, and an integrated circuit, where the integrated circuit includes a light source and light detector, where the integrated circuit is powered by the RF antenna. Here, the integrated circuit is powered by the RF antenna using RF energy harvesting. In one aspect the nano antenna is implantable to a human host.

According to a further aspect of the invention, the gold layer includes an electrically grounded gold layer, where the electrically grounded gold layer is configured to isolate the silica substrate and the gold nanodisk sensor to only be affected by a variation in blood properties, where the gold layer reflects refracted waves within the silica substrate and the silica disk back to the gold nano disk to enable constructive interference between an incident waves and the refracted waves.

In yet another aspect of the invention, a ratio of said silica disk to the gold nanodisk is in a range of 0.8 to 1.0.

In a further aspect of the invention, a height of the gold nanodisk is in a range of 50 nm to 200 nm.

According to one aspect of the invention, a diameter of the gold nanodisk is in a range of 400 nm to 600 nm to resonate at a wavelength of 1550 nm. This dimension can be scaled up or down for the device to resonate at higher or lower wavelength, respectively.

BRIEF DESCRIPTION OF THE DRAWINGS

FIG. 3. Shows the extinction spectrum of the prior art gold disk array on silica substrate for two different values of the refractive index of the surrounding medium, n=1.33 and n=1.34.

FIG. 4 shows a schematic drawing of the gold-silica disk nano antenna element, according to one embodiment of the invention.

FIGS. 10A-10C show the distribution of the electric field magnitude at 1554 nm along the x-z plane of the three disk sensors under investigation: (10A) gold disk, (10B) gold-silica disk, and (10C) gold-silica mushroom disk with e=0.8, according to the current invention.

DETAILED DESCRIPTION

The current invention provides novel designs of nano antenna arrays that are suitable for refractive index sensing. According to one embodiment, a single element design includes a gold disk placed on top of a silica disk with the same diameter. In another embodiment, the silica disk is etched radially-inward under the gold disk, which replicates a mushroom shape. The interaction between the analyte and the field concentration region of the gold disk is enhanced by adding the silica disk, and enhanced even more by etching this disk. This results in high sensitivity. The effects of the geometrical dimensions on the sensitivity are presented. These embodiments offer sensitivity as high as 1040 nm/RIU at 1554 nm resonance wavelength.

In one embodiment, a novel plasmonic nano sensor is provided that increases the sensitivity of the nano disk by placing a silica disk below it. Placing the silica disk increases the contact area of the analyte with the field surrounding the gold disk. This design overcomes the limitations of nano disk while keeping its height small. Through introducing radially-inward etching in the silica disk, the field-analyte area of contact increases even more, which in consequence increases the sensitivity of the structure. The effect of the gold and silica disks' heights, and the depth of inward-etching on the sensitivity are studied.

Figure 1A:
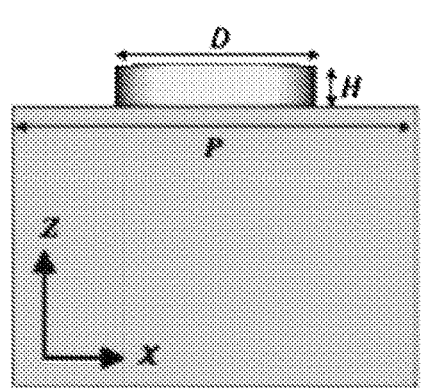
FIGS. 1A-1B show schematic drawings of the gold disk nano antenna element: (1A) side view, and (1B) top view, according to one embodiment of the invention.
Figure 1B:
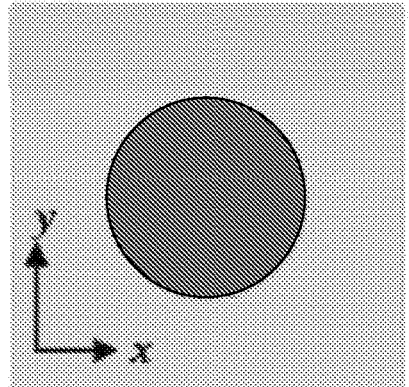
Figure 2:
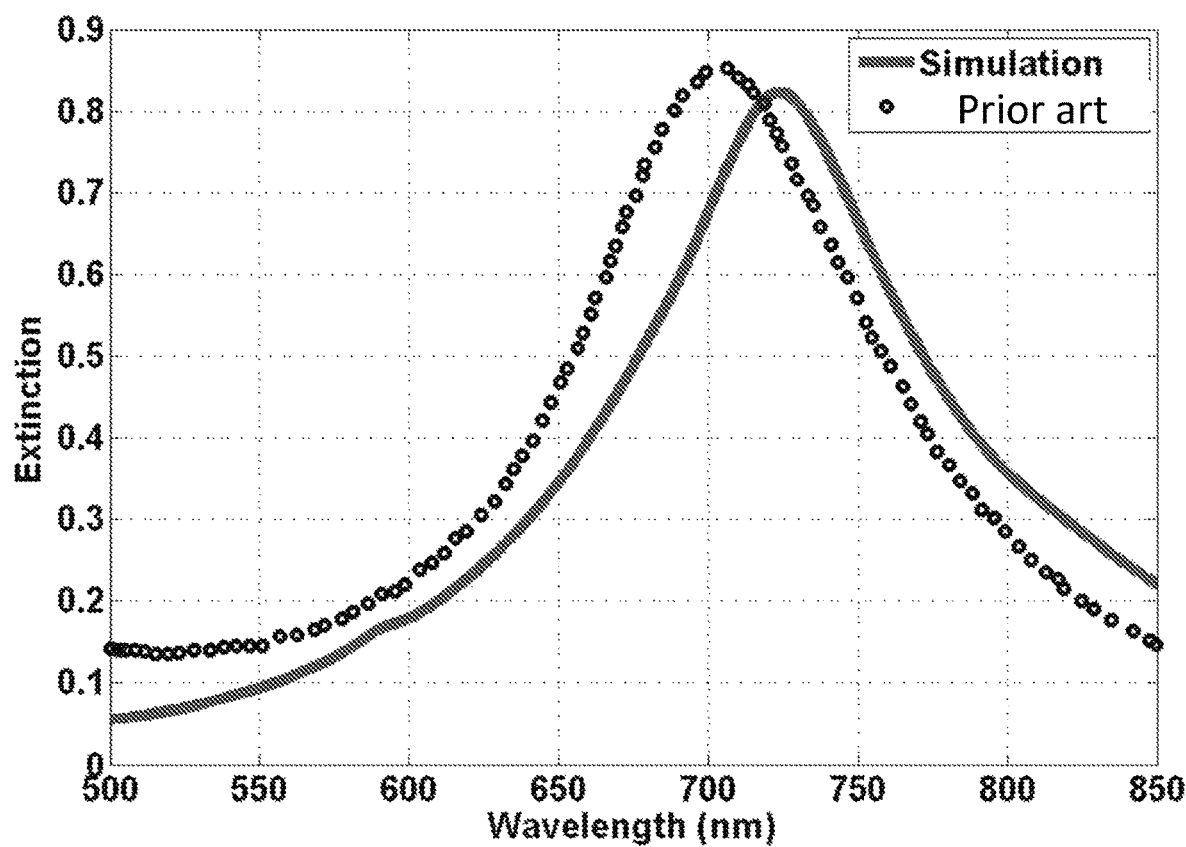
FIG. 2. Shows a comparison between the extinction spectrum of the simulated gold nano disk array structure according to the current invention and another sensor.

Gold disk nano antenna is one of the common structures used for sensing. Different studies were made to investigate its sensitivity. FIGS. 1A-1B show the schematic of a prior art gold disk nano antenna. The diameter and thickness of the gold disk are denoted by D and H, respectively. The disk is located on top of glass with refractive index of 1.52. An array of this element is realized with periodicity P. The referenced gold disk structure was replicated and simulated using the frequency-domain solver of CST Microwave Studio showing a good agreement with the prior art extinction spectrum as shown in FIG. 2.

By varying the refractive index of the surrounding medium, the sensitivity of the device can be calculated as the shift in the resonance wavelength per unit refractive index change. As shown in FIG. 2, the prior art gold nano disk structure has 137 nm diameter and 20 nm thickness was found to have a resonance wavelength around 700 nm. The periodicity of the nano disk array is 230 nm. The reported sensitivity of this nano disk is 200 nm/RIU. Scaling the dimensions of the nano disk to resonate in the near infrared regime, specifically at 1554 nm, the values of D, H, and P were found to be 492.5 nm, 100 nm, and 966 nm, respectively. The material of the substrate is changed from glass to silica due to its lower refractive index, which allows for more field concentration in the analyte region. FIG. 3 shows the extinction spectrum when the refractive index of the surrounding medium is changed from 1.33 to 1.34. As shown, the resonance wavelength is around 1554 nm as required, and the sensitivity increases to 500 nm/RIU. It is worth mentioning that as the resonance wavelength increases the sensitivity of the sensor increases because the near-field becomes more loosely bound to the gold surface, which allows for more interaction with the analyte leading to higher sensitivity.

Figure 9:
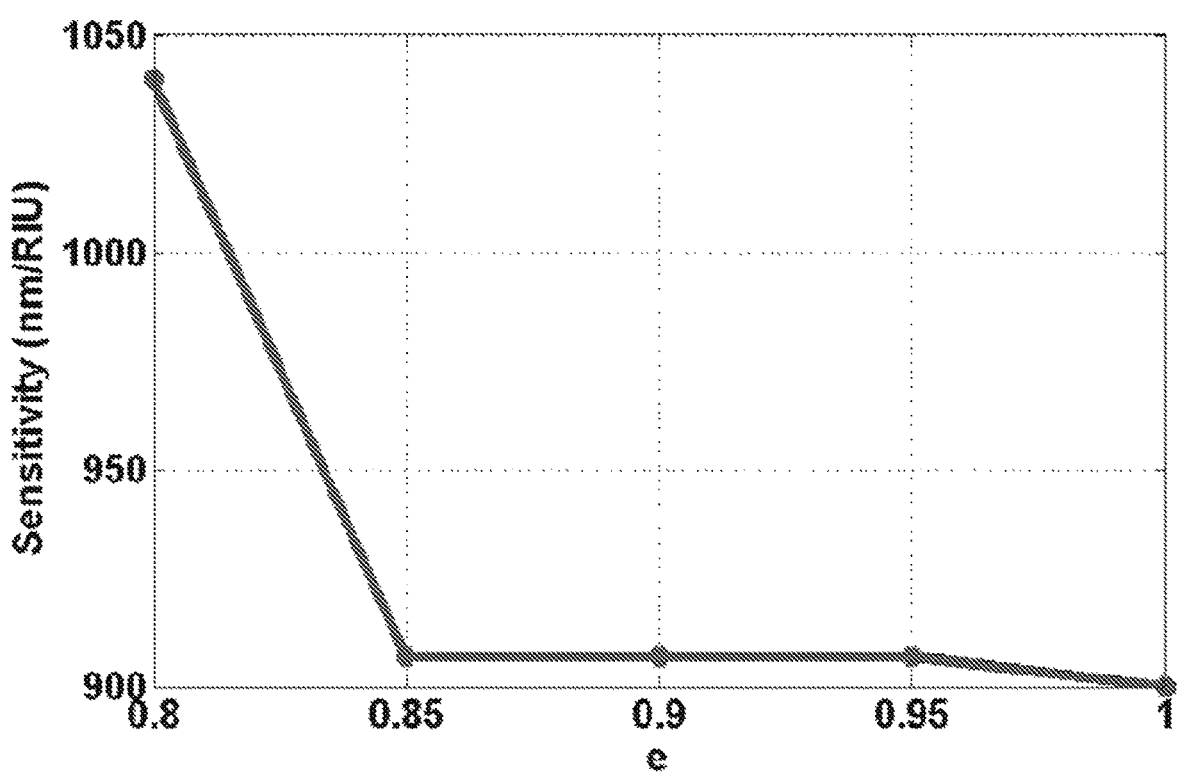
FIG. 9. shows the sensitivity of the mushroom gold-silica disk sensor versus e, according to one embodiment of the invention.

According to one embodiment of the current invention, by adding an extra silica disk below the gold disk as shown in FIG. 4, the contact area of the field concentration region with the analyte increases, stressing the analyte interaction with the oscillating electrons supported by the gold disk which enhances the sensitivity of the overall structure as will be illustrated later in the field distribution plots shown in FIG. 9. The silica and gold disks have the same diameter D, while their heights are denoted by H1 and H2, respectively.

Figure 5:
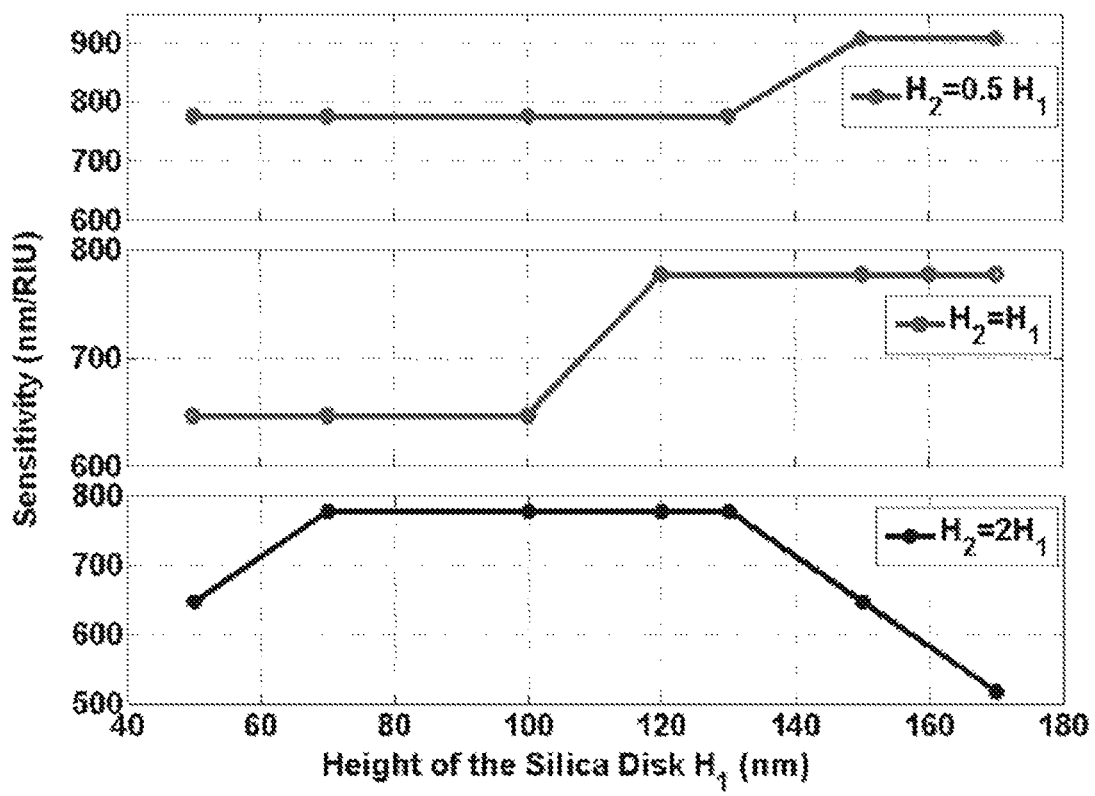
FIG. 5. shows the sensitivity of the gold-silica disk sensor versus H1 at different ratios of (H1 to H2), according to one embodiment of the invention.

The effect of varying the heights of the gold and silica disks is studied keeping the resonance wavelength of the structure at 1554 nm. FIG. 5 shows the sensitivity of the structure versus H1 at three different ratios of H2/H1: 0.5, 1 and 2. As shown, the sensitivity increases at large values of H1 when the thickness of the gold disk is smaller than or equal that of the silica disk. However, as the thickness of the gold disk becomes larger, the sensitivity decreases with the increase in H1. The maximum sensitivity obtained for this structure is 900 nm/RIU when H1 and H2 have the values 150 nm and 75 nm, respectively.

Figure 6A:
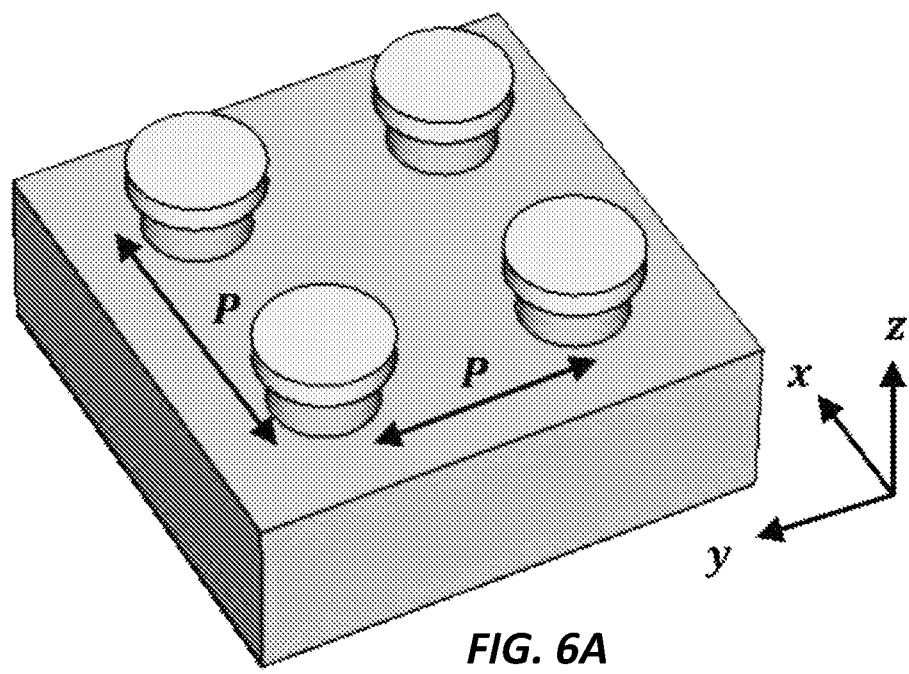
FIGS. 6A-6B show schematic drawings of the proposed array of mushroom gold-silica disk sensor with an etching ratio e=0.8: (6A) perspective view of the nano antenna array, and (6B) side view of the nano antenna unit cell with detailed geometry, according to one embodiment of the invention.
Figure 6B:
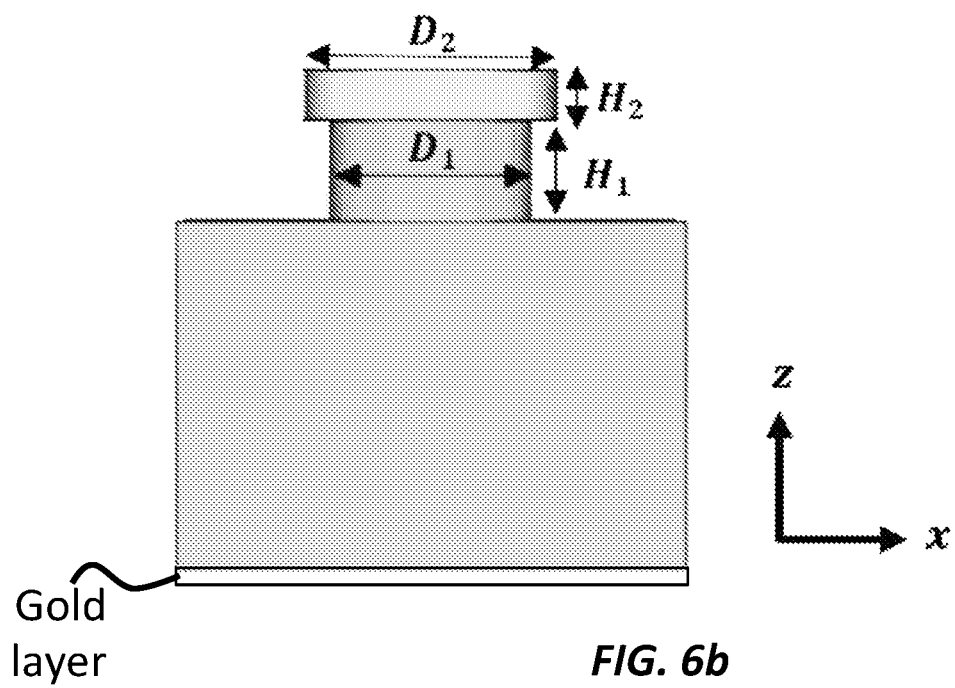

In order to further increase the interaction of the field concentration region with the analyte, radially-inward etching in the silica disk is provided. By decreasing the diameter of the silica disk to be smaller than that of the gold disk, more analyte can be in contact with the field maximum. FIG. 6 shows the schematic drawing of the mushroom sensor, where the silica disk below gold is radially-inward etched. The diameters of the silica and gold disks are now denoted by D1 and D2 respectively. The etching ratio is denoted by e where e=D1/D2.

In one aspect of the invention, a ratio of said silica disk to the gold nanodisk is in a range of 0.8 to 1.0. In a further aspect of the invention, a height of the gold nanodisk is in a range of 50 nm to 200 nm. According to one aspect of the invention, a diameter of the gold nanodisk is in a range of 400 nm to 600 nm to resonate at a wavelength of 1550 nm. This dimension can be scaled up or down for the device to resonate at higher or lower wavelength, respectively.

Figure 7:
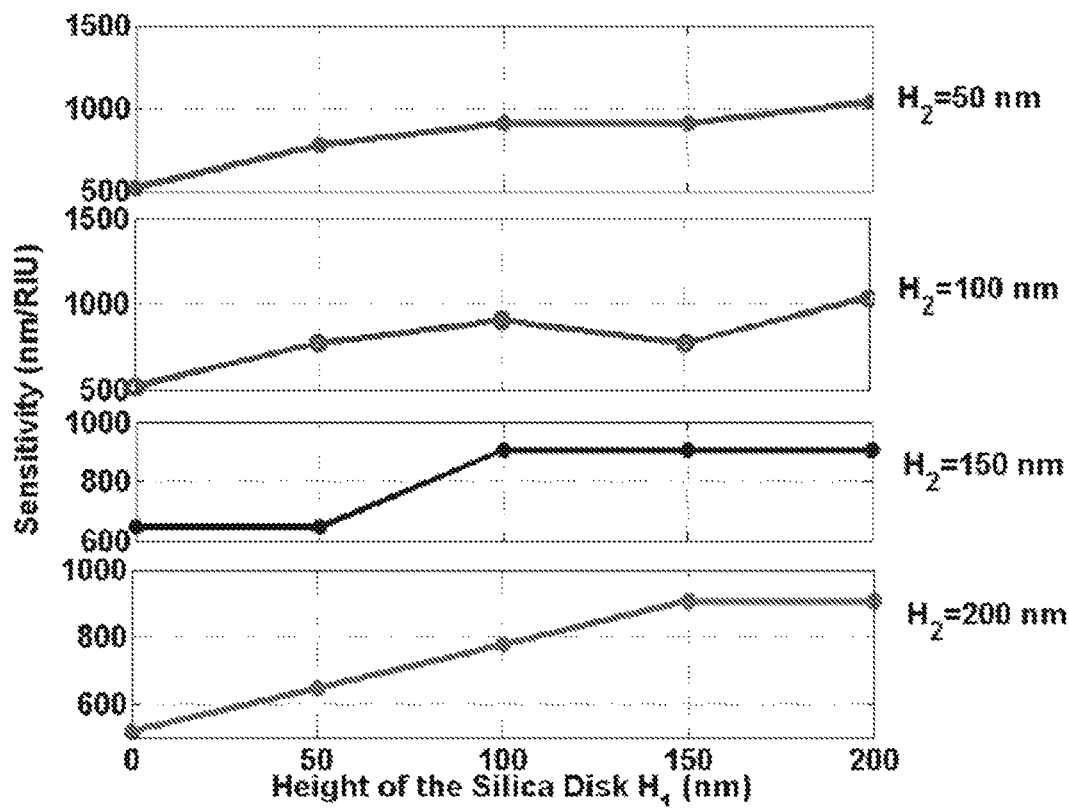
FIG. 7. shows the sensitivity of the mushroom gold-silica disk sensor with e=0.8 versus H1 at different values of H2.

The sensitivity of the mushroom gold-silica sensor is investigated. FIG. 7 presents the results of studying the effect of varying H1 and H2 on the sensitivity for an etching ratio e=0.8. As observed, the sensitivity increases as H1 increases for all values of H2. However, the maximum value of the sensitivity increases as H2 decreases.

Figure 8:
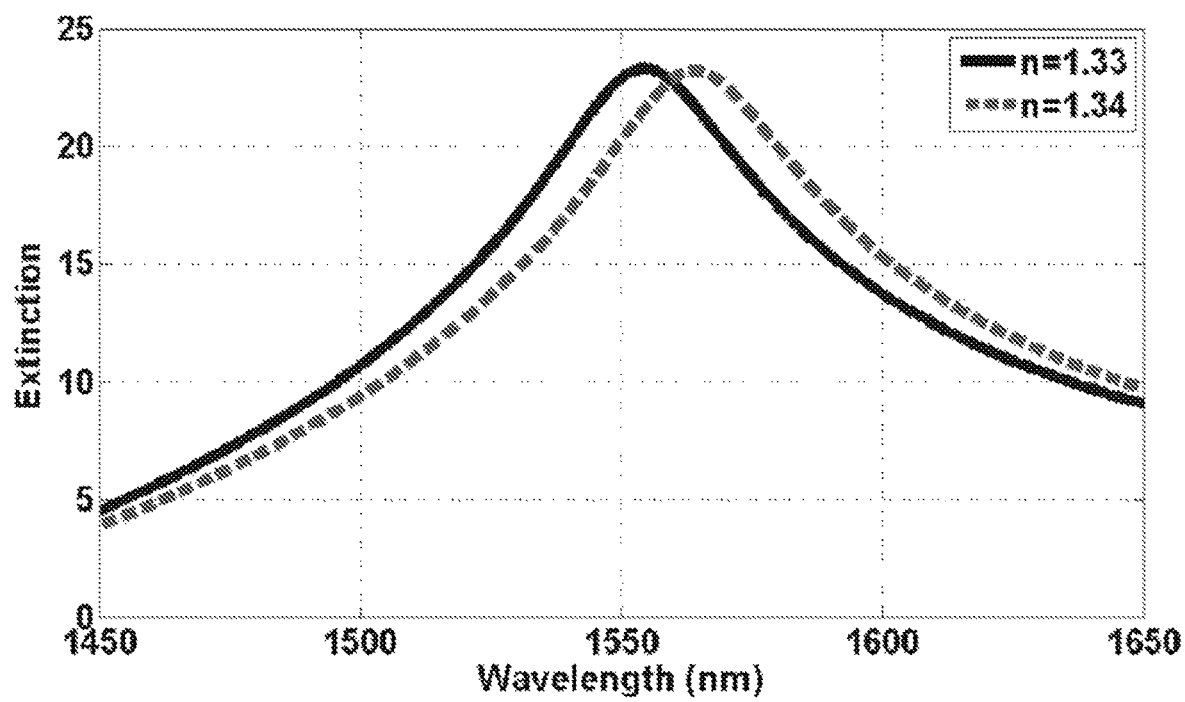
FIG. 8. shows the extinction spectrum of the mushroom gold-silica sensor with an etching ratio e=0.8 for two different values of the refractive index of the surrounding medium, n=1.33 and n=1.34 in which a sensitivity of 1040 nm/RIU is obtained, according to the current invention.

It is concluded that a maximum sensitivity of approximately 1040 nm/RIU is obtained at H1=200 nm and H2=100 nm and also at H1=200 nm and H2=50 nm. However, from the fabrication point of view, a gold thickness of 100 nm is more preferable than 50 nm. FIG. 8 shows the extinction spectrum of the optimum design for two different values of the refractive index of the surrounding medium.

Comparing FIG. 3 and FIG. 8, it becomes clear that the mushroom sensor offers significantly higher sensitivity than the basic disk sensor.

The effect of varying e on the sensitivity of the mushroom sensor is studied. The sensitivity was calculated for the structure at different etching ratios while keeping H1 and H2 at the optimum values concluded earlier for e=0.8. FIG. 9 shows the sensitivity of the structure versus e. It is concluded that the sensitivity of the structure increases as e decreases. In other words, as the radially-inward etching in the silica disk increases, the sensitivity of the mushroom gold-silica sensor increases. From the fabrication point of view, an etching ratio lower than 0.8 may affect the mechanical stability of the device. The maximum sensitivity at e=0.8 is 1040 nm/RIU.

A comparison between the electric field distributions for the three example embodiments is provided that include: gold disk, gold-silica disk, and mushroom gold-silica disk with e=0.8 is shown in FIGS. 10A-10C. It is clear from FIG. 10A that the field distribution is mainly localized around the edges of the gold disk. The field is partially confined inside the substrate. By inserting a silica disk below the gold disk, the field concentration area becomes in more contact with the analyte as shown in FIG. 10B, which increases the sensitivity of the structure. FIG. 10C displays the field distribution in case of etching the silica disk radially inward with an etching ratio of 0.8. As observed, this mushroom structure allows for more analyte interaction with the field concentration area around the gold disk leading to even more sensitivity. The dimensions of the three disk sensors under investigation together with their sensitivities are summarized in Table I.

TABLE I

SUMMARY OF DIMENSIONS AND SENSITIVITIES OF THE THREE NANO SENSORS UNDER INVESTIGATION.

| Design | $D_1$ (nm) | $D_2$ (nm) | P (nm) | $H_1$ (nm) | $H_2$ (nm) | Sensitivity (nm/RIU) |
|---|---|---|---|---|---|---|
| Gold Disk | — | 492.5 | 966 | — | 100 | 500 |
| Gold-Silica Disk | 492.6 | 492.6 | 966 | 150 | 75 | 900 |
| Gold-Silica Mushroom Disk (e = 0.8) | 403 | 503.5 | 987 | 200 | 100 | 1040 |

Figure 11:
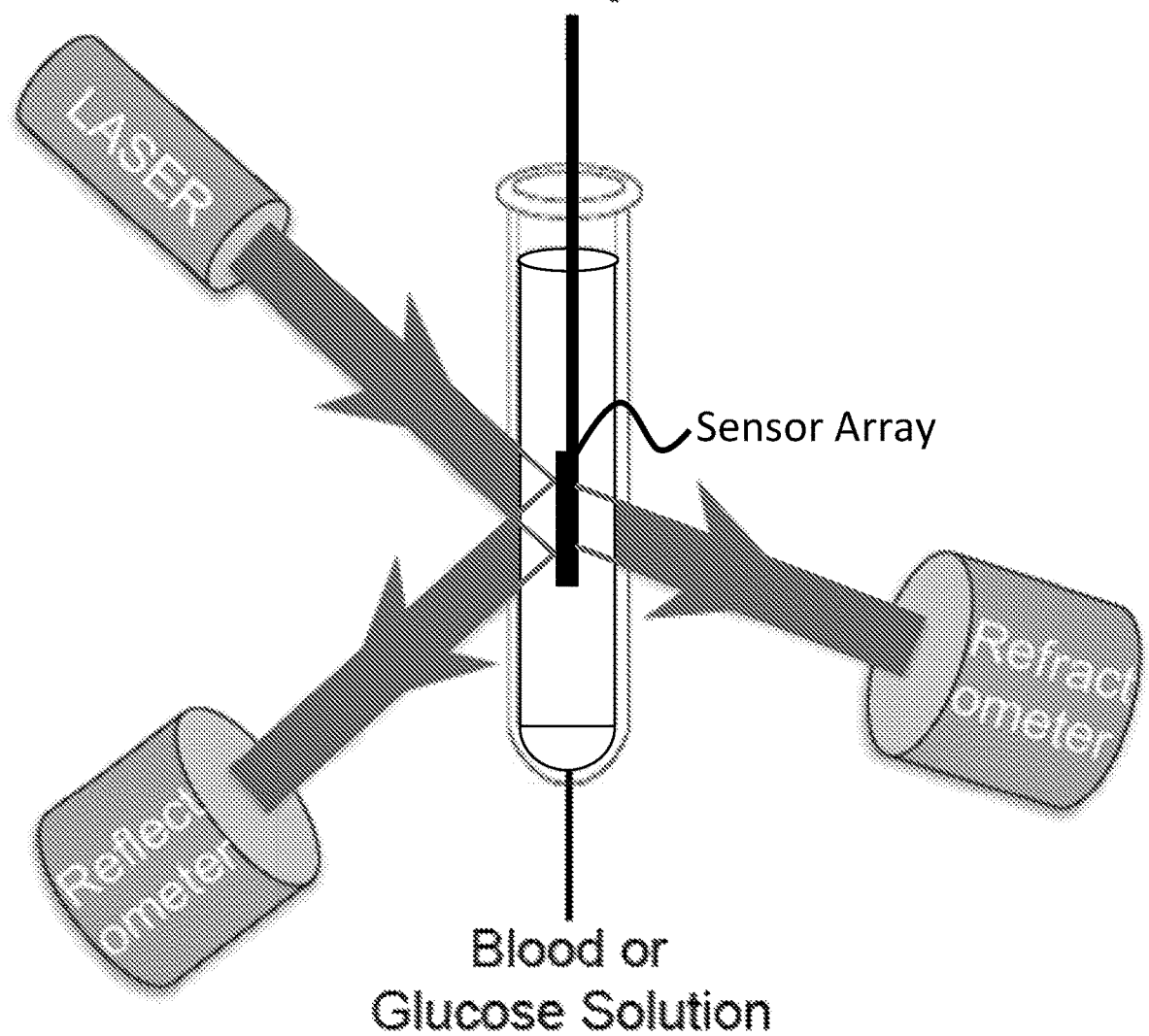
FIG. 11 shows a blood glucose sensor that uses an array of the mushroom sensors held by a fixture in a blood sample, according to one embodiment of the invention.

The current invention provides novel nano antenna designs for refractive index sensing. These designs overcome the limited sensitivity of gold nano disk sensors by placing a silica disk between the gold disk and the substrate. The effect of the heights of gold and silica disks on the sensitivity is presented, showing high sensitivity at small gold disk's height and large silica disk's height. It was demonstrated that radially inward etching of the silica disk increases the sensitivity even more due to more interaction between the field and the analyte. The structures according to the current invention are relatively low cost for fabrication as the minimum lateral dimension is 403 nm. The new sensors offer relatively high sensitivity that reaches 1040 nm/RIU at 1554 nm, which makes them attractive for biosensing applications. For example, FIG. 11 shows a blood glucose sensor that uses an array of the mushroom sensors held by a fixture in a blood sample. The sensors and sample are irradiated, using a laser for example, and the reflected and refracted light are measured to determine glucose levels in a blood sample.

Figure 12:
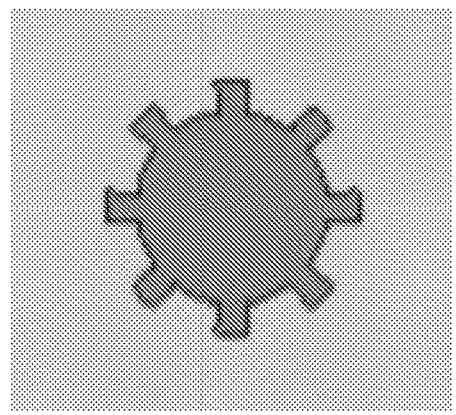
FIG. 12 shows the geometry of the gear nano gold disk that can replace the circular disk, according to one embodiment of the invention.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For example the circular gold disk can be replaced by a gear disk (see FIG. 12), which enhances the interaction between the field hot-spots and the surrounding medium whose refractive index is to be sensed. The geometry of the gear disk is shown in the figure below. This gear structure is promising as it provides better sensitivity than the circular disk. The dimensions of its three versions (without silica disk, with silica disk, and mushroom) are currently under optimization.

All such variations are considered to be within the scope and spirit of the present invention as defined by the following claims and their legal equivalents.

What is claimed is:

1. A nano antenna for refractive index sensing, comprising:
   a) a silica substrate;
   b) a gold nanodisk sensor element on a first side of said substrate, wherein said gold nanodisk sensor element comprises a silica disk disposed on said substrate and a gold disk disposed on said silica disk, wherein a diameter of said gold disk is greater than a diameter of said silica disk, wherein a height of said silica disk is greater than a height of said gold disk; and
   c) a gold layer disposed on a second side of said substrate opposite said first side, wherein said gold layer covers an area as large as said gold nanodisk sensor element.

2. The nano antenna according to claim 1, wherein said gold nanodisk sensor element comprises an array of said gold nanodisk sensor elements, wherein said gold layer covers an area at least as large as said array of gold nanodisk sensor elements.

3. The nano antenna according to claim 1 further comprises an RF antenna, and an integrated circuit, wherein said integrated circuit comprises a light source and light detector, wherein said integrated circuit is powered by said RF antenna.

4. The nano antenna according to claim 3, wherein said integrated circuit is powered by said RF antenna using RF energy harvesting.

5. The nano antenna according to claim 3, wherein said nano antenna is implantable to a human host.

6. The nano antenna according to claim 1, wherein said gold layer comprises an electrically grounded gold layer, wherein said electrically grounded gold layer is configured to isolate said silica substrate and said gold nanodisk sensor to only be affected by a variation in blood properties, wherein said gold layer reflects refracted waves within said silica substrate and said silica disk back to said gold nano disk to enable constructive interference between an incident waves and said refracted waves.

7. The nano antenna according to claim 1, wherein a ratio of the diameter of said silica disk to said gold nanodisk is in a range of 0.8 to 1.0.

8. The nano antenna according to claim 1, wherein a height of said gold nanodisk is in a range of 50 nm to 200 nm.

9. The nano antenna according to claim 1, wherein said diameter of said gold nanodisk is in a range of 400 nm to 600 nm to resonate at a wavelength of 1550 nm.

* * * * *